(12) United States Patent
Simon et al.

(10) Patent No.: US 8,313,730 B2
(45) Date of Patent: *Nov. 20, 2012

(54) TREATMENT OF CELIAC DISEASE WITH IGA

(75) Inventors: Michael R. Simon, Ann Arbor, MI (US); Mark Andrew Kroenke, Newbury Park, CA (US)

(73) Assignee: Michael R. Simon, Ann Arbor, MI (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/285,439

(22) Filed: Oct. 31, 2011

(65) Prior Publication Data

US 2012/0045517 A1 Feb. 23, 2012

Related U.S. Application Data

(63) Continuation-in-part of application No. 13/013,648, filed on Jan. 25, 2011, now Pat. No. 8,119,104, which is a continuation-in-part of application No. 12/138,758, filed on Jun. 13, 2008, now Pat. No. 8,021,645, which is a continuation-in-part of application No. 11/851,606, filed on Sep. 7, 2007, now Pat. No. 7,794,721, which is a continuation-in-part of application No. 11/839,781, filed on Aug. 16, 2007, now Pat. No. 7,597,891, which is a continuation-in-part of application No. 11/610,154, filed on Dec. 13, 2006, now abandoned.

(51) Int. Cl.
*A61K 49/00* (2006.01)
*A61K 39/395* (2006.01)
*A61K 39/40* (2006.01)

(52) U.S. Cl. .... 424/9.1; 424/9.2; 424/130.1; 424/134.1; 424/139.1; 424/141.1; 424/150.1

(58) Field of Classification Search .................. 424/9.1, 424/9.2, 130.1, 134.1, 139.1, 141.1, 150.1
See application file for complete search history.

(56) References Cited

U.S. PATENT DOCUMENTS

| | | | |
|---|---|---|---|
| 5,773,000 A | * | 6/1998 | Bostwick et al. .......... 424/167.1 |
| 2002/0110555 A1 | * | 8/2002 | Lee ........................... 424/130.1 |

* cited by examiner

*Primary Examiner* — Rodney P. Swartz
(74) *Attorney, Agent, or Firm* — Patent Procurement Services

(57) ABSTRACT

A process for inhibiting symptoms of a subject with celiac disease is provided that includes administration of monoclonal-, or polyclonal-, monomeric, dimeric, or polymeric IgA. Joining secretory component to the IgA limits oral administration degradation. Formulating agents are mixed with the monomeric, dimeric, or polymeric IgA to yield a dosing form of a capsule, tablet, and a suppository. The therapeutic is amenable to enrobement directly through microencapsulation or the dosing form is coated with an enteric coating.

16 Claims, No Drawings

TREATMENT OF CELIAC DISEASE WITH IGA

CROSS REFERENCE TO RELATED APPLICATIONS

This application is a continuation-in-part of U.S. patent application Ser. No. 13/013,648 filed Jan. 25, 2011, now U.S. Pat. No. 8,119,104; which in turn is a continuation-in-part of U.S. Patent application Ser. No. 12/138,758 filed Jun. 13, 2008, now U.S. Pat. No. 8,021,645 B2; which in turn is a continuation-in-part of U.S. patent application Ser. No. 11/851,606 filed Sep. 7, 2007, now U.S. Pat. No. 7,794,721; which in turn is a continuation-in-part of U.S. patent application Ser. No. 11/839,781 filed Aug. 16, 2007, now U.S. Pat. No. 7,597,891; which in turn is a continuation-in-part of U.S. patent application Ser. No. 11/610,154 filed Dec. 13, 2006 now abandoned. The contents of these applications are hereby incorporated by reference.

FIELD OF THE INVENTION

This invention relates in general to methods for the treatment of celiac disease and in particular to the treatment of celiac disease with orally administered immunoglobulin A (IgA), such as secretory IgA, and other IgA compositions administered in the form of pharmaceutical compositions.

BACKGROUND OF THE INVENTION

Celiac disease is an inherited, autoimmune disease in which the lining of the small intestine is damaged from eating gluten and other proteins found in wheat, barley, rye, and possibly oats. The symptoms of celiac disease can vary significantly from person to person. This is part of the reason the diagnosis is frequently delayed. For example, one person may have constipation, a second may have diarrhea, and a third may have no irregularity in stools. An endoscopy with enteroscopy, particularly of the distal small intestine which most commonly affected, reveals flattening of the villi.

Celiac disease is an enteropathy resulting from an abnormal immune response to gluten-derived peptides in genetically susceptible individuals. This immune response is initiated by intestinal transport of intact peptide 31-49 and 33-mer gliadin peptides. The transferrin receptor, CD71, is responsible for apical to basal retrotranscytosis of gliadin peptides. During this process peptide 31-49 and 33-mer peptides are protected from degradation. In patients with active celiac disease, CD71 is overexpressed in the intestinal epithelium and colocalizes with immunoglobulin (Ig) A. Intestinal transport of intact peptide 31-49 and 33-mer peptides is blocked by polymeric and secretory IgA. This retrotranscytosis of secretory IgA-gliadin complexes may promote the entry of harmful gliadin peptides into the intestinal mucosa. This may then initiate an immune response and perpetuate intestinal inflammation. These findings strongly implicate CD71 in the pathogenesis of celiac disease (Matysiak-Budnik T et al. 2008).

Treatment consists of adherence to a lifelong gluten-free diet. This allows the intestinal villi to heal. Foods, beverages, and medications that contain wheat, barley, and rye are eliminated. Wheat, rye, and barley are the grains that contain pathogenic peptides. Since wheat and barley comprise a major component of the American diet, this diet is difficult to adhere to.

Gastrointestinal symptoms in patients with symptomatic celiac disease who adhere to a gluten-free diet typically resolve within a few weeks. These patients experience the resolution of the findings of malnutrtion, improved growth with resultant normal stature, and normalization of blood and biochemical laboratory studies. Normal results from a follow-up endoscopy with biopsy several months after the diagnosis and treatment confirm the disease.

Thus, there exists a need for a therapeutic that is resistant to gastrointestinal tract degradation that is able to inhibit the symptoms of celiac disease in an afflicted subject. There also exists a need to provide such a therapeutic in a dosing form well suited for orally treating a celiac disease afflicted subject.

SUMMARY OF THE INVENTION

A process for inhibiting symptoms of a subject with celiac disease is provided that includes administration of mono- clonal- or polyclonal- , monomeric, dimeric or polymeric IgA therapeutic. Joining secretory component to the IgA limits oral administration degradation. Formulating agents are mixed with the monomeric, dimeric, or polymeric IgA to yield a dosing form of a capsule, tablet, and a suppository. The therapeutic is amenable to enrobement directly through microencapsulation or the dosing form is coated with an enteric coating.

DETAILED DESCRIPTION OF THE PREFERRED EMBODIMENTS

The present invention has utility as a treatment for celiac disease. While IgA levels have been reported to decrease in 2.8% of celiac disease patients, this decrease has been attributed to a disease process. IgA would not be used for treatment even in this patient population because intravenous IgA is known to cause anaphylaxis in patients with anti-IgA antibodies. The present invention is based on the surprising discovery that IgA at the mucosal surface, which can be achieved by oral dosing with an IgA formulation, is able to prevent retrotranscytosis of gliadin peptides associated with celiac disease and thereby disrupt the disease process. Administration of an IgA as a treatment for celiac disease has been disfavored as having no correlation with disease symptoms. Oral administration of IgA compositions as a treatment for an intestinal disease has been disfavored in the art out of concern that gastric degradation would further preclude an effective treatment. The method includes treatment with a monoclonal- or polyclonal- , monomeric, dimeric or polymeric IgA therapeutic. An inventive treatment is so provided through oral administration. The present invention uses monomeric IgA that is susceptible to gastrointestinal degradation, as well as dimeric and secretory IgA. Even with a degree of gastric degradation, sufficient quantities of an IgA can reach the affected intestinal epithelium. Because of its resistance to degradation in the gastrointestinal tract, secretory IgA is operative at lower doses relative to other forms of IgA. Dimeric IgA according to the present invention is bound to secretory component in order to mimic secretory IgA endogenous to the subject. In contrast to the conventional treatment for celiac disease which relies on a strict gluten free diet, an inventive treatment is provided that does not entail the severe limitation on the subject's diet.

As used herein, a "subject" is defined as humans and animal models for human disease.

The following description of the preferred embodiment(s) is merely exemplary in nature and is in no way intended to limit the invention, its application, or uses.

In one embodiment, the invention provides a method for medical treatment of humans involving the oral administration of secretory IgA which can be derived from a number of sources. One such source for the IgA is pooled human plasma following Cohn cold ethanol fractionation to produce fraction III precipitate as performed by those of skill in the art of protein separation. IgA byproduct is further purified by adsorption onto an ion exchange medium in neutral or slightly acidic conditions as performed by those of skill in the art of protein purification. Another source for the IgA is recombinant IgA produced from a hybridoma or a transgenic plant.

A more detailed description of isolation of an IgA component as a byproduct from pooled human plasma or hyperimmune pooled human plasma is as follows. Ethanol fractionation of pooled human plasma is a well-known process to prepare immunoglobulin G Pooled human plasma is first obtained from licensed plasmapheresis centers in the United States and tested for various pathogens including the HIV virus. The first manufacturing step of most commercial immunoglobulin G preparations involves a modified cold ethanol fractionation according to Cohn to produce Cohn fraction II. In the fractionation process, many infectious viruses are eliminated from the pooled human plasma. Following fractionation, the Cohn fraction II is subjected to adsorption onto an ion exchange medium. This step may selectively reduce the IgA concentration to less than 0.1%. Such a step is important for producing immunoglobulin G for intravenous infusion into humans. This is because some individuals undergo an anaphylactic-like reaction if treated with intravenous IgG that contains IgA as an impurity.

The modified cold ethanol fractionation process according to Cohn is a series of fractionations using various levels of ethanol, pH, and temperature to produce a fraction II which is further treated to produce immunoglobulins as described above. In the fractionation method, pooled human plasma is first treated to produce a cryoprecipitate and cryo-supernatant. The cryo-supernatant is subjected to a first ethanol fractionation to yield a supernatant I. Supernatant I is subjected to a second ethanol fractionation to yield fraction II+III. Fraction II+III is subjected to a third ethanol fractionation procedure to yield a supernatant III and Fraction III precipitate.

The fraction III precipitate enriched in IgA is generally discarded as an unwanted byproduct. According to the invention, this unwanted IgA following ion exchange adsorption purification is further treated by incubation with immobilized hydrolases to inactivate viruses and vasoactive substances. Such treatment has been proven to eliminate many viruses tested including HIV, Sindbis, and vaccinia. Other antiviral treatments, as known to those skilled in the art, are used in combination and consist of solvent detergent processes, nanofiltration and/or heat inactivation. Usually three antiviral steps are implemented. Following incubation to remove viruses, the concentration of the active material is adjusted with sterile saline or buffered solutions to ensure a constant amount of active material per milliliter of reconstituted product. Finally, the solution with a constant amount of reconstituted product is sterilized by filtration before use.

The ethanol fractionation process according to Cohn is well known in the art and is described in Cohn et al., J. Am. Chem. Soc. 1946; 68:459-475, Oncley et al., J. Am. Chem. Soc. 1949; 71:541-550, and in most detail in pages 576-602, Kirk-Othmer Encyclopedia of Chemical Technology, Vol. 3, second edition (1963). Alternatively, ion exchange chromatography may be used to obtain the dimeric and polymeric IgA byproduct during the manufacture of intravenous immunoglobulin. From 4% to 22% of plasma IgA is dimeric and polymeric IgA (Delacroix et al. J. Clin. Invest. 1982 August; 70(2): 230-41; Delacroix et al., J. Clin. Invest. 1983 February; 71(2):358-67). The resulting dimeric and polymeric IgA-J chains are purified.

In a preferred embodiment, the compositions of the invention contain, in addition to the IgA component, a recombinant secretory component. Human secretory component can be produced by recombinant techniques as described in Crottet et al., Biochem. J. 1999; 341:299-306. The resulting dimeric IgA is further coupled to recombinant secretory component. In a preferred embodiment, the coupling is accomplished by forming disulfide bonds under mildly oxidizing conditions. (Jones R. M. L., Schweikart F., Frutiger S., Jaton J-C., Hughes G. J. Thiol-disulfide redox buffers maintain a structure of immunoglobulin A that is essential for optimal in vitro binding to secretory component. Biochimica et Biophysica Acta 1998; 1429:265-274.) Dimeric IgA containing both J chain and secretory component is again purified by ion-exchange and size exclusion chromatography and/or ultrafiltration as described in Lullau et al., J. Biol. Chem. 1996; 271: 16300-16309, Corthesy, Biochem. Soc. Trans. 1997; 25:471-475, and Crottet et al., Biochem. J. 1999; 341:299-306, as performed by those of skill in the art of protein purification. Purified dimeric and polymeric IgA containing secretory component is optionally stabilized for example by the addition of human serum albumin to a final concentration of 5%. The presence of the human J chains and secretory component in the compositions of the invention leads to doses of immunoglobulin A which are more physiologically effective than compositions without such components. Dimeric IgA contains two IgA monomers per J chain.

The secretory IgA antibodies are administered alone as a liquid or solid, preferably in a solid powder form and preferably in admixture with a carrier to form a pharmaceutical composition such as a tablet, capsule or suppository.

The present invention also provides a process for medical treatment of humans involving the oral administration of monomeric or dimeric IgA which can be derived from pooled human plasma or monoclonal IgA which can be derived by hybridoma technology (B Cell Design, Limoge, France).

Since preferred methods of administration are oral with solid oral dosage forms such as tablets and capsules being especially preferred, or enteric installation. These are prepared according to conventional methods known to those skilled in the art. The secretory IgA antibodies may also be combined with other pharmaceutically acceptable carriers such as various liquids, proteins or oils which may also provide additional nutritional and/or pharmaceutical benefits. Remington Science and Practice of Pharmacy, $20^{th}$ ed. (2000).

These compositions optionally contain adjuvants such as preserving, wetting, emulsifying, and dispensing agents. Prevention of the action of microorganisms can be ensured by various antibacterial and antifungal agents, for example, parabens, chlorobutanol, phenol, sorbic acid, and the like. It may also be desirable to include isotonic agents, for example, sugars, sodium chloride, and the like. Prolonged absorption of the IgA can be brought about by the use of agents delaying absorption, for example, aluminum monostearate and gelatin.

Solid dosage forms for oral administration include capsules, tablets, pills, powders, and granules. In such solid dosage forms, the active compound is admixed with at least one inert customary excipient (or carrier) such as sodium citrate or dicalcium phosphate or (a) fillers or extenders, as for example, starches, lactose, sucrose, glucose, mannitol, and silicic acid, (b) binders, as for example, carboxymethylcellulose, alignates, gelatin, polyvinylpyrrolidone, sucrose, and acacia, (c) humectants, as for example, glycerol, (d) disintegrating agents, as for example, agar-agar, calcium carbonate, potato or tapioca starch, alginic acid, certain complex silicates, and sodium carbonate, (e) solution retarders, as for example, paraffin, (f) absorption accelerators, as for example, quaternary ammonium compounds, (g) wetting agents, as for example, cetyl alcohol, and glycerol monostearate, (h) adsorbents, as for example, kaolin and bentonite, and (i) lubricants, as for example, talc, calcium stearate, magnesium stearate, solid polyethylene glycols, sodium lauryl sulfate, or mixtures thereof. In the case of capsules, tablets, and pills, the dosage forms may also comprise buffering agents.

Solid compositions of a similar type may also be employed as fillers in soft and hard-filled gelatin capsules using such excipients as lactose or milk sugar as well as high molecular weight polyethyleneglycols, and the like.

Solid dosage forms such as tablets, dragees, capsules, pills, and granules can be prepared with coatings and shells, such as enteric coatings and others well known in the art; as detailed, for example in U.S. Pat. Nos. 4,017,647; 4,385,078; 4,518,433; and 4,556,552.

They may contain opacifying agents, and can also be of such composition that they release the active compound or compounds in a certain part of the intestinal tract in a delayed manner. Examples of embedding compositions which can be used are polymeric substances and waxes. The active compounds can also be in microencapsulated form, if appropriate, with one or more of the above-mentioned excipients.

Liquid dosage forms for oral administration include pharmaceutically acceptable emulsions, solutions, suspensions, syrups, and elixirs. In addition to the active compounds, the liquid dosage forms may contain inert diluents commonly used in the art, such as water or other solvents, solubilizing agents and emulsifiers, as for example, ethyl alcohol, isopropyl alcohol, ethyl carbonate, ethyl acetate, benzyl alcohol, benzyl alcohol, benzyl benzoate, propyleneglycol, 1,3-butyleneglycol, dimethylformamide, oils, in particular, cottonseed oil, groundnut oil, corn germ oil, olive oil, castor oil and sesame oil, glycerol, tetrahydrofurfuryl alcohol, polyethyleneglycols and fatty acid esters of sorbitan or mixtures of these substances, and the like.

Besides such inert diluents, the composition can also include adjuvants, such as wetting agents, emulsifying and suspending agents, sweetening, flavoring, and perfuming agents.

Suspensions, in addition to the active compounds, may contain suspending agents, as for example, ethoxylated isostearyl alcohols, polyoxyethylene sorbitol and sorbitan esters, microcrystalline cellulose, aluminum metahydroxide, bentonite, agar-agar and tragacanth, or mixtures of these substances, and the like.

Since the effect of the secretory IgA antibody is dependent on its reaching the small intestine, preferred tablets or capsules are enteric coated. Alternatively, the active secretory IgA antibodies can themselves be microencapsulated prior to formulation. Preparation of microcapsules of secretory IgA antibody as well as preparation of enteric coated tablets or capsules can be achieved by conventional methods as detailed above.

The amount of an IgA effective to treatment symptoms of celiac disease is appreciated to be dependent on the form and route of administration, as well as the extent of the disease as manifestation by CD71 intestinal epithelium expression. As detailed herein, secretory IgA is administered in lower doses orally to be effective relative to other forms thereof. The amount of an orally administered secretory IgA provided to the patient is about 0.001 to 50 grams per day. Preferably, 0.1 to 10 grams per day are administered with dosings of up to an order of magnitude being typical for non-secretory forms of IgA. For example, dosings of IgA could be given to a subject 3 to 4 times per day. The doses of the IgA antibody formulation to be administered will depend upon the subject and the subject's medical history. Dosages of IgA for adult humans envisioned by the present invention and considered to be therapeutically effective will range from between about 0.1 to 500 mg. However, it is to be understood that doses can readily be adjusted to provide appropriate amounts of the IgA antibody to any subject, including children.

The invention is further described by reference to the following detailed examples, wherein the methodologies are as described below. These examples are not meant to limit the scope of the invention that has been set forth in the foregoing description. Variations within the concepts of the invention are apparent to those skilled in the art.

EXAMPLE 1

Polyclonal IgA is obtained from pooled human plasma following Cohn cold ethanol fractionation to produce fraction III precipitate. IgA is further purified by adsorption onto an ion exchange medium in neutral or slightly acidic conditions. IgA-J chain dimers and polymers are purified. IgA-J chain dimers and polymers are then further coupled to recombinant secretory component again by disulfide bonding in mildly oxidizing conditions, preferably at a molar ratio of secretory component to IgA-J chain dimers and polymers of 1:1. IgA containing both J chain and secretory component is again purified. Purified IgA containing J chain and secretory component is stabilized by the addition of human serum albumin to a final concentration of 5%. The final solution is adjusted to a therapeutic dose of 5 mg IgA. The IgA is administered to a person suffering with celiac disease. One month after initiation of treatment the celiac disease sufferer eats gluten without inducing any symptoms of intestinal dysfunction. A biopsy of the small intestine reveals that the appearance of the villi has returned to normal.

EXAMPLE 2

The process of Example 1 is repeated with only the IgA-J chain dimers coupled to secretory component, stabilized by the addition of human serum albumin to a final concentration of 5%. The final solution is adjusted to a therapeutic dose of 5 mg IgA. The IgA is administered to a person suffering with celiac disease. One month after initiation of treatment the celiac disease sufferer eats gluten without inducing any symptoms of intestinal dysfunction. A biopsy of the small intestine reveals that the appearance of the villi has returned to normal.

EXAMPLE 3

The process of Example 1 is repeated with only the IgA-J chain polymers coupled to secretory component, stabilized by the addition of human serum albumin to a final concentration of 5%. The final solution is adjusted to a therapeutic dose of 5 mg IgA. The IgA is administered to a person suffering with celiac disease. One month after initiation of treatment the celiac disease sufferer eats gluten without inducing any symptoms of intestinal dysfunction. A biopsy of the small intestine reveals that the appearance of the villi has returned to normal.

EXAMPLE 4

The process of Example 1 is repeated with only the IgA-J chain dimers without secretory component, stabilized by the addition of human serum albumin to a final concentration of 5%. The final solution is adjusted to a therapeutic dose of 10 mg IgA. The IgA is administered to a person suffering with celiac disease. One month after initiation of treatment the celiac disease sufferer eats gluten without inducing any symptoms of intestinal dysfunction. A biopsy of the small intestine reveals that the appearance of the villi has returned to normal.

EXAMPLE 5

The process of Example 1 is repeated with only the IgA-J chain polymers without secretory component, stabilized by the addition of human serum albumin to a final concentration of 5%. The final solution is adjusted to a therapeutic dose of 10 mg IgA. The IgA is administered to a person suffering with celiac disease. One month after initiation of treatment the celiac disease sufferer eats gluten without inducing any symptoms of intestinal dysfunction. A biopsy of the small intestine reveals that the appearance of the villi has returned to normal.

EXAMPLE 6

Monoclonal monomeric IgA is obtained from hybridoma technology. The monoclonal IgA is stabilized by the addition of human serum albumin to a final concentration of 5% and administered without encapsulation. The final solution is adjusted to a therapeutic dose of 20 mg IgA daily. The IgA is administered to a person suffering with celiac disease. One month after initiation of treatment the celiac disease sufferer eats gluten without inducing any symptoms of intestinal dysfunction. A biopsy of the small intestine reveals that the appearance of the villi has returned to normal.

EXAMPLE 7

The process of Example 6 is repeated with the IgA administered with an enteric, encapsulating coating and a lower daily dose of 5 mg to achieve a similar result.

EXAMPLE 8

The process of Example 6 is repeated with dimeric IgA administered with an enteric, encapsulating coating and a lower daily dose of 5 mg to achieve a similar result

REFERENCES

Marietta E, Black K, Camilleri M, Krause P, Rogers R S 3rd, David C, Pittelkow M R, Murray J A. A new model for dermatitis herpetiformis that uses HLA-DQ8 transgenic NOD mice. J Clin Invest. 2004 October;114(8):1090-7.

Matysiak-Budnik T, Moura I C, Arcos-Fajardo M, Lebreton C, Ménard S, Candalh C, Ben-Khalifa K, Dugave C, Tamouza H, van Niel G Bouhnik Y, Lamarque D, Chaussade S, Malamut G, Cellier C, Cerf-Bensussan N, Monteiro R C, Heyman M. Secretory IgA mediates retrotranscytosis of intact gliadin peptides via the transferrin receptor in celiac disease. J Exp Med. 2008 Jan. 21;205(1): 143-54.

Berzofsky J. A., Berkower I. J., Epstein S. L., Monoclonal Antibodies in Chapter 12, Antigen-Antibody Interactions and Monoclonal Antibodies, pp. 455-465 in Fundamental Immunology, Third Edition, W. E. Paul (ed), Raven Press, N.Y. 1993. Berzofsky et al., Fundamental Immunology, Third Edition, 1993, pp 455-462.

Cohn E. J., Strong L. E., Hughes W. L., Jr., Mulford D. J., Ashworth J. N., Melin M., Taylor H. L., Preparation and Properties of Serum and Plasma Proteins IV. A System for the Separation into Fractions of the Protein and Lipoprotein Components of Biological Tissues and Fluids, J. Am. Chem. Soc. 1946; 68;459-475.

Corthesy B., Recombinant Secretory IgA for Immune Intervention Against Mucosal Pathogens, Biochem. Soc. Trans. 1997, 25;471-475.

Crottet P., Cottet S., Corthesy B., Expression, Purification and Biochemical Characterization of Recombinant Murine Secretory Component, A Novel Tool in Mucosal Immunology, Biochem. J. 1999, 341;299-306.

Delacroix D. L., Hodgson H. J., McPherson A., Dive C., Vaerman J. P. Selective transport of polymeric immunoglobulin A in bile. Quantitative relationships of monomeric and polymeric immunoglobulin A, immunoglobulin M, and other proteins in serum, bile, and saliva. J. Clin. Invest. 1982 August;70(2):230-41

Delacroix D. L., Elkom K. B., Geubel A. P., Hodgson H. F., Dive C., Vaerman J. P. Changes in size, subclass, and metabolic properties of serum immunoglobulin A in liver diseases and in other diseases with high serum immunoglobulin A. J. Clin. Invest. 1983 February;71(2):358-67.

Jones R. M. L., Schweikart F., Frutiger S., Jaton J-C., Hughes G J. Thiol-disulfide redox buffers maintain a structure of immunoglobulin A that is essential for optimal in vitro binding to secretory component. Biochimica et Biophysica Acta 1998; 1429:265-274.

Kohler G, Milstein C., Continuous Cultures of Fused Cells Secreting Antibody of Predetermined Specificity, Nature 1975; 256;495-497.

Lullau E., Heyse S., Vogel H., Marison I., von Stockar U., Kraehanbuhl J-P., Corthesy B., Antigen Binding Properties of Purified Immunoglulin A Antibodies, J. Biol. Chem. 1996; 271:16300-16309.

Oncley J. L., Melin M., Richert D. A., Cameron J. W., Gross P. M., Jr., The Separation of the Antibodies, Isoagglutinins, Prothrombin, Plasminogen and β1-Lipoprotein into Subfractions of Human Plasma. J. Am. Chem. Soc. 1949; 71:541-550.

Strong L. E., Blood Fractionation, pp. 576-602 in vol. 3, Kirk-Othmer Encyclopedia of Chemical Technology. Second Edition, H. F. Mark, J. J. McKetta, D. F. Othmer (eds), Interscience Publishers, N.Y. 1963, pp. 576-602.

Symersky J., Novak J., McPherson D. T., DeLucas L., Mestecky J. Expression of the recombinant human immunoglobulin J chain in *Escherichia coli*. Mol. Immunol. 2000; 37:133-140.

Patent applications and publications mentioned in the specification are indicative of the levels of those skilled in the art to which the invention pertains. These applications and publications are incorporated herein by reference to the same extent as if each individual application or publication was specifically and individually incorporated herein by reference.

The foregoing description is illustrative of particular embodiments of the invention, but is not meant to be a limitation upon the practice thereof. The following claims, including all equivalents thereof, are intended to define the scope of the invention.

The invention claimed is:

1. A process for inhibiting symptoms of celiac disease in a subject comprising:
   orally administering an IgA selected from the group consisting of IgA monomers, dimeric IgA consisting of two IgA monomers and a J chain, and polymeric IgA to the subject suffering from celiac disease in a dosage of greater than 0.1 milligrams per day; and allowing sufficient time for inhibiting symptoms of celiac disease in that subject.

2. The process of claim 1, wherein said IgA is polyclonal.

3. The process of claim 2, wherein said IgA is said IgA monomer.

4. The process of claim 2, wherein said IgA is said dimeric IgA.

5. The process of claim 2, wherein said IgA is said polymeric IgA.

6. The process of claim 2, wherein said IgA is recombinant.

7. The process of claim 2 further comprising secretory component wherein said IgA is polymeric IgA.

8. The process of claim 1, wherein said IgA is monoclonal.

9. The process of claim 8, wherein said IgA is said IgA momomer.

10. The process of claim 8, wherein said IgA is said dimeric IgA.

11. The process of claim 8, wherein said IgA is said polymeric IgA.

12. The process of claim 8, wherein said IgA is recombinant.

13. The process of claim 8 further comprising secretory component wherein said IgA is polymeric IgA.

14. The process of claim 1 wherein said IgA is administered as a tablet or a capsule.

15. The process of claim 1 further comprising combining an excipient with said IgA to yield a dosing form selected from the group consisting of: a solid oral dosing form, a liquid oral dosing form, and a suppository.

16. The process of claim 1 wherein said IgA is administered orally.

* * * * *